United States Patent
Olbrich et al.

(10) Patent No.: US 9,308,284 B2
(45) Date of Patent: *Apr. 12, 2016

(54) FORMULATIONS OF FLUORINATED STILBENE SUITABLE FOR PET IMAGING

(75) Inventors: Carsten Olbrich, Berlin (DE); Michael Krause, Berlin (DE); Andreas Burkhard, Falkensee (DE); Annett Richter, Berlin (DE); Rainer Braun, Berlin (DE)

(73) Assignee: PIRAMAL IMAGING SA, Matran (CH)

( * ) Notice: Subject to any disclaimer, the term of this patent is extended or adjusted under 35 U.S.C. 154(b) by 23 days.

This patent is subject to a terminal disclaimer.

(21) Appl. No.: 14/128,015

(22) PCT Filed: Jun. 21, 2012

(86) PCT No.: PCT/EP2012/062034
§ 371 (c)(1),
(2), (4) Date: Apr. 7, 2014

(87) PCT Pub. No.: WO2012/175641
PCT Pub. Date: Dec. 27, 2012

(65) Prior Publication Data
US 2014/0241986 A1    Aug. 28, 2014

(30) Foreign Application Priority Data

Jun. 21, 2011  (EP) .................................... 11005047

(51) Int. Cl.
| | | |
|---|---|---|
| A61K 51/00 | (2006.01) | |
| A61M 36/14 | (2006.01) | |
| A61K 51/04 | (2006.01) | |
| A61K 9/00 | (2006.01) | |
| A61K 47/10 | (2006.01) | |
| A61K 47/22 | (2006.01) | |
| A61K 49/00 | (2006.01) | |

(52) U.S. Cl.
CPC ............ *A61K 51/0497* (2013.01); *A61K 9/0019* (2013.01); *A61K 47/10* (2013.01); *A61K 47/22* (2013.01); *A61K 49/0004* (2013.01); *A61K 51/04* (2013.01)

(58) Field of Classification Search
None
See application file for complete search history.

(56) References Cited

U.S. PATENT DOCUMENTS

| | | |
|---|---|---|
| 7,807,135 B2 | 10/2010 | Kung et al. |
| 7,902,144 B2 | 3/2011 | Kratz |
| 8,465,726 B2 | 6/2013 | Kung et al. |
| 2003/0185793 A1 | 10/2003 | Kratz |
| 2006/0269473 A1 | 11/2006 | Kung et al. |
| 2010/0172836 A1* | 7/2010 | Benedum et al. ............ 424/1.89 |
| 2010/0266500 A1 | 10/2010 | Kung et al. |
| 2011/0142759 A1* | 6/2011 | Zhang et al. ................. 424/1.89 |
| 2013/0059564 A1 | 3/2013 | Jung et al. |
| 2013/0059565 A1 | 3/2013 | Jung et al. |
| 2013/0209363 A1 | 8/2013 | Berndt et al. |

FOREIGN PATENT DOCUMENTS

| | | |
|---|---|---|
| WO | 01/68142 A1 | 9/2001 |
| WO | 2006/066104 A2 | 6/2006 |
| WO | 2011/074825 A2 | 6/2011 |
| WO | 2011/151283 A1 | 12/2011 |

OTHER PUBLICATIONS

Klok et al. Appl. Rad. Isot. 2008, 66, 203-207.*
International Search Report dated Aug. 2, 2012 issued in corresponding PCT/EP2012/062034 application (pp. 1-4).
S.R. Choi et al., "Preclinical Properties of 18F-AV-45: A PET Agent for Abeta Plaques in the Brain", The Journal of Nuclear Medicine, vol. 50, No. 11 (2009) pp. 1887-1894.
R.G. Strickley, "Solubilizing Excipients in Oral and Injectable Formulations", Pharmaceutical Research, vol. 21, No. 2 (Feb. 2004) pp. 201-230.

* cited by examiner

*Primary Examiner* — Michael G Hartley
*Assistant Examiner* — Sean R Donohue
(74) *Attorney, Agent, or Firm* — Millen White Zelano and Branigan, PC; John Sopp; Anthony Zelano

(57) ABSTRACT

The invention is directed to formulations of lipophilic Amyloid beta ligand stilbene and more particularly to formulations which are capable to be administered parenterally e.g. intravenously, wherein the lipophilic Amyloid beta ligand stilbene is a fluorinated stilbene. Further, the invention is directed to a method for sterile filtration of formulations suitable for PET imaging of mammals pursuant to the invention.

4 Claims, No Drawings

FORMULATIONS OF FLUORINATED STILBENE SUITABLE FOR PET IMAGING

FIELD OF THE INVENTION

The invention is directed to formulations of lipophilic Amyloid beta ligand stilbene and more particularly to formulations, which are capable to be administered parenterally e.g. intravenously, wherein the lipophilic Amyloid beta ligand stilbene is a fluorinated stilbene as defined below. Further, the invention is directed to a method for sterile filtration of pharmaceutical formulations pursuant to the invention suitabl9:31 AM 3/10/2016e for PET imaging of mammals.

BACKGROUND

Stilbene useful for Positron Emission Tomography (PET) imaging of patient are known from WO2003/018070A1 and WO2006/066104A1. Stilbene are radiolabeled with $^{18}F$ radioisotope whereas radiolabeling occurred in organic solution in presence of the stilbene precursor and $[^{18}F]$. The stilbene precursor can be in a dry condition and optionally has an inert pharmaceutically acceptable carrier and/or auxiliary substances added thereto and a reducing agent and optionally a chelator. The fluoro-radiolabeled stilbene (PET tracer) solution may contain any additive such as pH controlling agents (e.g. acids, bases, buffers), stabilizers (e.g. ascorbic acid) or isotonizing agents (e.g. sodium chloride).

Ethanol, isopropanol, glycerol, and polyethylene glycol are well known as solubility-increasing excipients, WO2001/68142.

Usually, PET supply centers produce on demand a hot stock solution comprising the pharmaceutical that is injected to the patient along the working day. The hot stock solution must be stable and storable. Furthermore, a significant amount of newly synthesised PET tracer is lost during purification step(s) i.e. sterile filtration. Until now, there has been little published on formulations suitable for PET-pharmaceuticals.

Thus, there is a need for commercially acceptable suitable formulations comprising a PET agent, characterized in that the PET agent shows a low water solubility i.e. lipophilic PET agent, wherein the PET agent is an Amyloid beta ligand stilbene useful for PET imaging.

It has been surprisingly found that the claimed pharmaceutical formulation is chemically stable and can be stored at least for 8 hours and that this pharmaceutical formulation allows the sterile filtration using suitable filter material(s) without loss of activity.

It has been found that fluoro-radiolabeled stilbene are solubilized and stabilized by the formulation of present invention. Using this formulation, dilutions needed for adjustment of activity can be made in a wide range of dilution ratios, allowing the precise adjustment for any patient at any given time of the shelf life. It combines good local tolerability with easy applicability within the manufacturing process for the radio-labeled PET tracer.

Sterile filtration step is necessary for providing a sterile parenteral pharmaceutical formulation and the like for obtaining a suitable pharmaceutical solution for pharmaceutical use. Unfortunately, a critical loss of PET tracer is in many cases observed. Thus, there is a need for improving the purification steps leading to an increase of the radio-labelling yield.

It has been surprisingly found that the pharmaceutical formulation of the present invention is successfully used with a sterile filter reducing adsorption onto a sterile filter of the pharmaceutical.

SUMMARY

The invention is directed to formulations of lipophilic Amyloid beta ligand stilbene and more particularly to formulations, which are capable to be administered parenterally e.g. intravenously, wherein the lipophilic Amyloid beta ligand stilbene is a $^{18}F$-labeled pharmaceutical thereof. Further, the invention is directed to a method for sterile filtration of said pharmaceutical formulation.

DETAILED DESCRIPTION

The present invention concerns formulations comprising pharmaceuticals e.g. radiotracer, wherein the pharmaceutical formulation is suitable for parenteral administration into mammals.

In a first aspect, the invention is directed to pharmaceutical formulations comprising:
  Lipophilic Amyloid beta ligand stilbene and suitable salts thereof,
  Ethanol,
  Polyether,
  Ascorbic acid, and
  Sodium ascorbate.

Preferably, the invention is directed to pharmaceutical formulations comprising:
  0.03 GBq/mL to 5 GBq/mL Lipophilic Amyloid beta ligand stilbene when F is $^{18}F$ or 0.01 µg/mL to 5 µg/mL Lipophilic Amyloid beta ligand stilbene and suitable salts thereof,
  8% v/v to 25% v/v Ethanol,
  10% w/v to 25% w/v Polyether,
  0.01% to 3% w/v Ascorbic acid, and
  0.01% to 20% w/v Sodium ascorbate.

Lipophilic Amyloid Beta Ligand Stilbene:

The term stilbene as used herein, refers to compounds of formula A

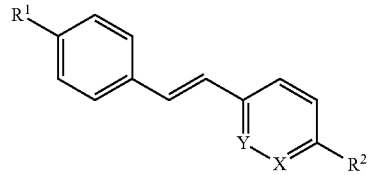

Formula A wherein,
X is selected from the group comprising C and N,
Y is selected from the group comprising C and N,
$R^1$ is $NR^3R^4$,
preferably, $R^3$ is $(C_1-C_4)$alkyl,
preferably, $R^4$ is selected from the group comprising H and Boc (tert-butoxycarbonyl),
$R^2$ is selected from the group comprising $(O-CH_2CH_2)_nF$, $(O-CH_2)_n-OR^5$, OH,
preferably, $R^5$ is selected from the group comprising H, $O-SO_2-R^6$,
n is selected from the group comprising 1, 2, 3 and 4.
preferably, $R^1$ is $NHCH_3$, and/or
preferably, $(O-CH_2)_n-F$ and/or preferably, Y=C and/or
preferably, X=C and/or
preferably, n=3 and/or More preferably, lipophilic Amyloid beta ligand stilbene is Methyl-[4-((F)-2-{4-[2-(2-ethoxy-ethoxy)-ethoxy]-phenyl}-vinyl)-phenyl]-amine wherein F is fluorine atom that is $^{18}$F or $^{19}$F and suitable salts thereof.

Even more preferably, Lipophilic Amyloid beta ligand stilbene is Methyl-[4-((F)-2-{4-[2-(2-ethoxy-ethoxy)-ethoxy]-phenyl}-vinyl)-phenyl]-amine according to Figure 1 below or Methyl-[4-(($^{18}$F)-2-{4-[2-(2-ethoxy-ethoxy)-ethoxy]-phenyl}-vinyl)-phenyl]-amine according to Figure 2 below.

Fig. 1 Compound 1

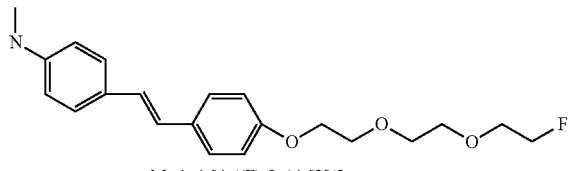

Methyl-[4-((F)-2-{4-[2[(2-propoxy-ethoxy)-ethoxy]-phenyl}-vinyl)-phenyl]-amine

Fig. 2 Compound 2

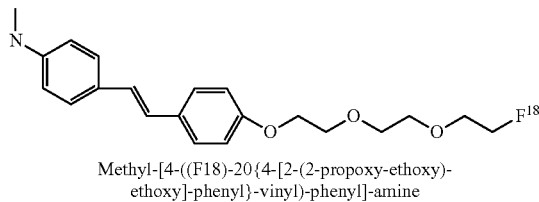

Methyl-[4-((F18)-20{4-[2-(2-propoxy-ethoxy)-ethoxy]-phenyl}-vinyl)-phenyl]-amine Preferably, the compound 1 according to Figure 1 or compound 2 according to Figure 2 or a mixture thereof is present in the pharmaceutical formulation in an amount of about 0.01 µg/mL to 5 µg/mL, more preferably in an amount of about 0.01 to 3.5 µg/mL. Even more preferably, compound 1 or 2 or a mixture thereof is/are present in the pharmaceutical formulation in an amount of about 3 µg/mL.

When F is $^{18}$F, then the lipophilic Amyloid beta ligand stilbene is a PET tracer present in the pharmaceutical formulation pursuant to the invention at the dose of 0.03 GBq/mL to 5 GBq/mL, preferably 0.03 GBq/mL to 3 GBq/mL.

Ethanol:
In a preferred embodiment, ethanol is present in the pharmaceutical formulation in an amount of about 8% v/v to 30% v/v. Preferably, the ethanol is present in a maximum amount of 25% v/v or 20% v/v. More preferably, the ethanol is present in an amount of about 10% v/v to 15% v/v, more preferably 15% v/v. Preferably, the ethanol is a 96% up to 100% ethanol. Preferably, ethanol is in an amount of about 15% v/v.

Polyether:
In a preferred embodiment, the polyether is present in the pharmaceutical formulation in an amount of about 10% w/v to 25% w/v. Preferably, the polyether is present in an amount of about 10% w/v to 20% w/v, more preferably 20% w/v. Polyether is preferably a poly(ethylene glycol) (PEG), such as PEG 300, PEG 400 or PEG 1500.

Preferably, polyether is PEG 400 in an amount of about 20% w/v.

Ascorbic Acid:
In a preferred embodiment, ascorbic acid is present in the pharmaceutical formulation in an amount of 0.01% to 3% w/v. Preferably, ascorbic acid is present in an amount of about 0.01% w/v to 1.5% w/v, more preferably is present in an amount of about 0.44% w/v.

Sodium Ascorbate:
In a preferred embodiment, sodium ascorbate is present in the pharmaceutical formulation in an amount of 0.01% to 20% w/v. Preferably, sodium ascorbate is present in an amount of about 1.5% w/v to 5% w/v, more preferably is present in an amount of about 2.88% w/v.

Preferably, the invention is directed to pharmaceutical formulations comprising:
Lipophilic Amyloid beta ligand stilbene and suitable salts thereof,
Ethanol,
Poly(ethylene glycol),
Ascorbic acid, and
Sodium ascorbate.

More preferably, the invention is directed to pharmaceutical formulations comprising:
Methyl-[4-((F)-2-{4-[2-(2-ethoxy-ethoxy)-ethoxy]-phenyl}-vinyl)-phenyl]-amine or Methyl-[4-(($^{18}$F)-2-{4-[2-(2-ethoxy-ethoxy)-ethoxy]-phenyl}-vinyl)-phenyl]-amine or mixture thereof, and suitable salts thereof,
Ethanol,
Poly(ethylene glycol),
Ascorbic acid, and
Sodium ascorbate.

Even more preferably, the invention is directed to pharmaceutical formulations comprising:
0.03 GBq/mL to 5 GBq/mL Methyl-[4-(($^{18}$F)-2-{4-[2-(2-ethoxy-ethoxy)-ethoxy]-phenyl}-vinyl)-phenyl]-amine and suitable salts thereof,
8% v/v to 25% v/v Ethanol,
10% w/v to 25% w/v Poly(ethylene glycol),
0.01% to 3% w/v Ascorbic acid, and
0.01% to 20% w/v Sodium ascorbate.

Even more preferably, the invention is directed to pharmaceutical formulations comprising:
0.03 GBq/mL to 5 GBq/mL Methyl-[4-(($^{18}$F)-2-{4-[2-(2-ethoxy-ethoxy)-ethoxy]-phenyl}-vinyl)-phenyl]-amine and suitable salts thereof,
10% v/v to 15% v/v Ethanol,
10% w/v to 20% w/v Poly(ethylene glycol),
0.01% to 1.5% w/v Ascorbic acid, and
1.5% to 5% w/v Sodium ascorbate.

Even more preferably, the invention is directed to pharmaceutical formulations comprising:
0.03 GBq/mL to 5 GBq/mL Methyl-[4-(($^{18}$F)-2-{4-[2-(2-ethoxy-ethoxy)-ethoxy]-phenyl}-vinyl)-phenyl]-amine and suitable salts thereof,
15% v/v Ethanol,
20% w/v PEG 400,
0.44% w/v Ascorbic acid, and
2.88% w/v Sodium ascorbate.

Even more preferably, the invention is directed to pharmaceutical formulations comprising:
0.01 µg/mL to 5 µg/mL Methyl-[4-((F)-2-{4-[2-(2-ethoxy-ethoxy)-ethoxy]-phenyl}-vinyl)-phenyl]-amine or mixture of Methyl-[4-((F)-2-{4-[2-(2-ethoxy-ethoxy)-ethoxy]-phenyl}-vinyl)-phenyl]-amine and Methyl-[4-(($^{18}$F)-2-{4-[2-(2-ethoxy-ethoxy)-ethoxy]-phenyl}-vinyl)-phenyl]-amine, and suitable salts thereof,
8% v/v to 25% v/v Ethanol,
10% w/v to 25% w/v Poly(ethylene glycol),
0.01% to 3% w/v Ascorbic acid, and
0.01% to 20% w/v Sodium ascorbate.

Even more preferably, the invention is directed to pharmaceutical formulations comprising:

0.01 μg/mL to 5 μg/mL Methyl-[4-((F)-2-{4-[2-(2-ethoxy-ethoxy)-ethoxy]-phenyl}-vinyl)-phenyl]-amine or mixture of Methyl-[4-((F)-2-{4-[2-(2-ethoxy-ethoxy)-ethoxy]-phenyl}-vinyl)-phenyl]-amine and Methyl-[4-(($^{18}$F)-2-{4-[2-(2-ethoxy-ethoxy)-ethoxy]-phenyl}-vinyl)-phenyl]-amine, and suitable salts thereof,
10% v/v to 15% v/v Ethanol,
10% w/v to 20% w/v Poly(ethylene glycol),
0.01% to 1.5% w/v Ascorbic acid, and
1.5% to 5% w/v Sodium ascorbate.

Even more preferably, the invention is directed to pharmaceutical formulations comprising:

3 μg/mL Methyl-[4-((F)-2-{4-[2-(2-ethoxy-ethoxy)-ethoxy]-phenyl}-vinyl)-phenyl]-amine or mixture of Methyl-[4-((F)-2-{4-[2-(2-ethoxy-ethoxy)-ethoxy]-phenyl}-vinyl)-phenyl]-amine and Methyl-[4-(($^{18}$F)-2-{4-[2-(2-ethoxy-ethoxy)-ethoxy]-phenyl}-vinyl)-phenyl]-amine, and suitable salts thereof,
15% v/v Ethanol,
20% w/v PEG 400,
0.44% w/v Ascorbic acid, and
2.88% w/v Sodium ascorbate.

Preferably, the pharmaceutical formulation comprises a mixture of compounds 1 and 2 according to FIGURES 1 and 2 or a mixture of suitable salts thereof.

The formulations of the present invention are pharmaceutical formulations suitable for parenteral administration into mammals for conducting PET imaging.

The pharmaceutical formulation has a pH of about 4.5 to 8.5, preferably 5 to 6, which is suitable for injection in patient.

In a second aspect, the invention is directed to a method for preparing the pharmaceutical formulations of the present invention comprising a lipophilic Amyloid beta ligand stilbene by general Formula A, or the Figures 1 and 2 as set out below.

Lipophilic Amyloid Beta Ligand Stilbene:

The term stilbene as used in the second aspect, refers to compounds of formula A Formula A

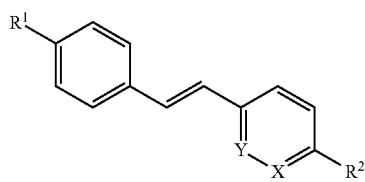

wherein,
X is selected from the group comprising C and N,
Y is selected from the group comprising C and N,
$R^1$ is $NR^3R^4$,
preferably, $R^3$ is $(C_1-C_4)$alkyl,
preferably, $R^4$ is selected from the group comprising H and Boc (tert-butoxycarbonyl),
$R^2$ is selected from the group comprising $(O—CH_2CH_2)_nF$, $(O—CH_2)_n—OR^5$, OH,
preferably, $R^5$ is selected from the group comprising H, $O—SO_2—R^6$,
n is selected from the group comprising 1, 2, 3 and 4.
preferably, $R^1$ is $NHCH_3$, and/or
preferably, $(O—CH_2)_n—F$ and/or
preferably, Y=C and/or preferably, X=C and/or
preferably, n=3 and/or More preferably, lipophilic Amyloid beta ligand stilbene is Methyl-[4-((F)-2-{4-[2-(2-ethoxy-ethoxy)-ethoxy]-phenyl}-vinyl)-phenyl]-amine wherein F is fluorine atom that is $^{18}$F or $^{19}$F and suitable salts thereof.

Even more preferably, Lipophilic Amyloid beta ligand stilbene is Methyl-[4-((F)-2-{4-[2-(2-ethoxy-ethoxy)-ethoxy]-phenyl}-vinyl)-phenyl]-amine according to Figure 1 below or Methyl-[4-(($^{18}$F)-2-{4-[2-(2-ethoxy-ethoxy)-ethoxy]-phenyl}-vinyl)-phenyl]-amine according to Figure 2 below.

Fig. 1 Compound 1

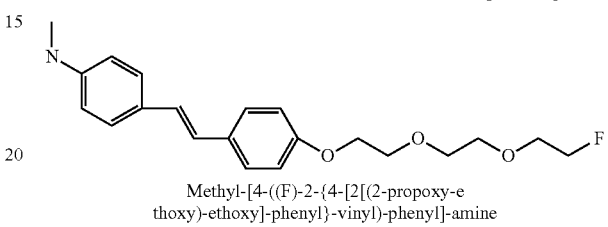

Methyl-[4-((F)-2-{4-[2[(2-propoxy-ethoxy)-ethoxy]-phenyl}-vinyl)-phenyl]-amine

Fig. 2 Compound 2

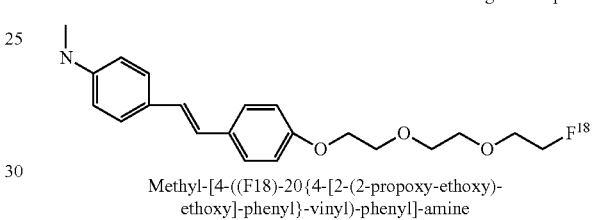

Methyl-[4-((F18)-20{4-[2-(2-propoxy-ethoxy)-ethoxy]-phenyl}-vinyl)-phenyl]-amine Preferably, the lipophilic Amyloid beta ligand stilbene is a Methyl-[4-((F)-2-{4-[2-(2-ethoxy-ethoxy)-ethoxy]-phenyl}-vinyl)-phenyl]-amine wherein F is fluorine atom that is $^{18}$F or $^{19}$F or mixture thereof.

The method comprises the steps of:
Solubilisation of lipophilic Amyloid beta ligand stilbene in ethanol,
Adding the ethanol solution of first step into a mixture of polyether, ascorbic acid, and sodium ascorbate.

Embodiments disclosed above for lipophilic Amyloid beta ligand stilbene according to the general Formula A, and the Figures 1 and 2, ethanol, polyether, ascorbic acid, and sodium ascorbate are included within the below context of a method for preparation.

Preferably, the method comprises the steps of:
Solubilisation of
Methyl-[4-((F)-2-{4-[2-(2-ethoxy-ethoxy)-ethoxy]-phenyl}-vinyl)-phenyl]-amine or mixture of Methyl-[4-((F)-2-{4-[2-(2-ethoxy-ethoxy)-ethoxy]-phenyl}-vinyl)-phenyl]-amine and Methyl-[4-(($^{18}$F)-2-{4-[2-(2-ethoxy-ethoxy)-ethoxy]-phenyl}-vinyl)-phenyl]-amine in ethanol, and
Adding the ethanol solution of first step into a mixture of polyether, ascorbic acid, and sodium ascorbate.

More preferably, the method comprises the steps of:
Solubilisation of 3 μg/mL of
Methyl-[4-((F)-2-{4-[2-(2-ethoxy-ethoxy)-ethoxy]-phenyl}-vinyl)-phenyl]-amine or mixture of Methyl-[4-((F)-2-{4-[2-(2-ethoxy-ethoxy)-ethoxy]-phenyl}-vinyl)-phenyl]-amine and Methyl-[4-(($^{18}$F)-2-{4-[2-(2-ethoxy-ethoxy)-ethoxy]-phenyl}-vinyl)-phenyl]-amine in ethanol, and
Adding the ethanol solution of first step into a mixture of PEG 400, ascorbic acid, and sodium ascorbate resulting in a final concentration of 15% v/v ethanol, 20% w/v PEG 400, 0.44% w/v ascorbic acid, and 2.88% w/v sodium ascorbate.

In a third aspect, the invention is directed to a method for sterile filtration of the pharmaceutical formulations of the present invention comprising a lipophilic Amyloid beta ligand stilbene according to the general Formula A, and according to Figures 1 and 2 as set out below.

Lipophilic Amyloid Beta Ligand Stilbene:

The term stilbene as used in the third aspect, refers to compounds of formula A

Formula A wherein,

X is selected from the group comprising C and N,

Y is selected from the group comprising C and N, $R^1$ is $NR^3R^4$, preferably, $R^3$ is $(C_1-C_4)$alkyl, preferably, $R^4$ is selected from the group comprising H and Boc (tert-butoxycarbonyl), $R^2$ is selected from the group comprising $(O-CH_2CH_2)_nF$, $(O-CH_2)_n-OR^5$, OH, preferably, $R^5$ is selected from the group comprising H, $O-SO_2-R^6$, n is selected from the group comprising 1, 2, 3 and 4.

preferably, $R^1$ is $NHCH_3$, and/or preferably, $(O-CH_2)_n-F$ and/or preferably, Y=C and/or preferably, X=C and/or preferably, n=3 and/or More preferably, lipophilic Amyloid beta ligand stilbene is Methyl-[4-((F)-2-{4-[2-(2-ethoxy-ethoxy)-ethoxy]-phenyl}-vinyl)-phenyl]-amine wherein F is fluorine atom that is $^{18}F$ or $^{19}F$ and suitable salts thereof.

Even more preferably, Lipophilic Amyloid beta ligand stilbene is Methyl-[4-((F)-2-{4-[2-(2-ethoxy-ethoxy)-ethoxy]-phenyl}-vinyl)-phenyl]-amine according to Figure 1 below or Methyl-[4-(($^{18}F$)-2-{4-[2-(2-ethoxy-ethoxy)-ethoxy]-phenyl}-vinyl)-phenyl]-amine according to 2 below.

Fig. 1 Compound 1

Methyl-[4-((F)-2-{4-[2[(2-propoxy-ethoxy)-ethoxy]-phenyl}-vinyl)-phenyl]-amine

Fig. 2 Compound 2

Methyl-[4-((F18)-20{4-[2-(2-propoxy-ethoxy)-ethoxy]-phenyl}-vinyl)-phenyl]-amine Preferably, the lipophilic Amyloid beta ligand stilbene is Methyl-[4-((F)-2-{4-[2-(2-ethoxy-ethoxy)-ethoxy]-phenyl}-vinyl)-phenyl]-amine wherein F is fluorine atom that is $^{18}F$ or $^{19}F$ or mixture thereof.

It was surprisingly found that the adsorption onto sterile filter is strongly decreased when the pharmaceutical formulation of the present invention is used. The sterile filter can be standard sterile filter used for radiotracer filtration. Such sterile filters are well known in the art.

The method for sterile filtration of the pharmaceutical formulations of the present invention comprises the step of giving the pharmaceutical formulation of the present invention onto a sterile filter.

The lipophilic Amyloid beta ligand stilbene according to the general Formula A, and the Figures 1 and 2 as described above are hydrophobic substances and the claimed pharmaceutical formulations allow the dissolution of the substances at the required doses. It is well known and acknowledged that hydrophobic filters have an affinity for hydrophobic substances. It was surprisingly found that the pharmaceutical formulations of the present invention prevent this adsorption and allows a high yield sterile filtration.

Preferably, the method for sterile filtration of the pharmaceutical formulations of the present invention comprises the step of giving the pharmaceutical formulation of the present invention onto polytetrafluoroethylene (PTFE) sterile filter e.g. Sartorius Minisart 0.2 µm (Order number 16596) or Polyvinylidene Fluoride (PVDF) sterile filter e.g. Millipore Millex 0.2 µm SLGV033RS.

More preferably, the hydrophobic filter is polytetrafluoroethylene (PTFE) sterile filter.

Optionally, the sterile filtration method is preceded by the preparation of the pharmaceutical formulation of the present invention.

Embodiments disclosed above for the lipophilic Amyloid beta ligand stilbene according to general Formula A, and the Figures 1 and 2, ethanol, polyether, ascorbic acid, and sodium ascorbate are also included within the below context of the fourth, fifth and sixth aspect as follows:

Lipophilic Amyloid Beta Ligand Stilbene:

The term stilbene as used within the context of the below fourth, fifth, and sixth aspect of the invention, refers to compounds of formula A Formula A wherein,
X is selected from the group comprising C and N,
Y is selected from the group comprising C and N,
$R^1$ is $NR^3R^4$,
preferably, $R^3$ is $(C_1\text{-}C_4)$alkyl,
preferably, $R^4$ is selected from the group comprising H and Boc (tert-butoxycarbonyl),
$R^2$ is selected from the group comprising $(O\text{—}CH_2CH_2)_nF$, $(O\text{—}CH_2)_n\text{—}OR^5$, OH,
preferably, $R^5$ is selected from the group comprising H, $O\text{—}SO_2\text{—}R^6$,
n is selected from the group comprising 1, 2, 3 and 4.
preferably, $R^1$ is $NHCH_3$, and/or
preferably, $(O\text{—}CH_2)_n\text{—}F$ and/or
preferably, Y=C and/or
preferably, X=C and/or
preferably, n=3 and/or
More preferably, lipophilic Amyloid beta ligand stilbene is Methyl-[4-((F)-2-{4-[2-(2-ethoxy-ethoxy)-ethoxy]-phenyl}-vinyl)-phenyl]-amine wherein F is fluorine atom that is $^{18}F$ or $^{19}F$ and suitable salts thereof.
Even more preferably, Lipophilic Amyloid beta ligand stilbene is Methyl-[4-((F)-2-{4-[2-(2-ethoxy-ethoxy)-ethoxy]-phenyl}-vinyl)-phenyl]-amine according to Figure 1 below or Methyl-[4-(($^{18}F$)-2-{4-[2-(2-ethoxy-ethoxy)-ethoxy]-phenyl}-vinyl)-phenyl]-amine according to Figure 2 below.

Fig. 1 Compound 1

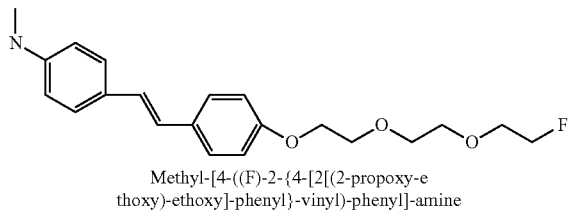

Methyl-[4-((F)-2-{4-[2[(2-propoxy-ethoxy)-ethoxy]-phenyl}-vinyl)-phenyl]-amine

Fig. 2 Compound 2

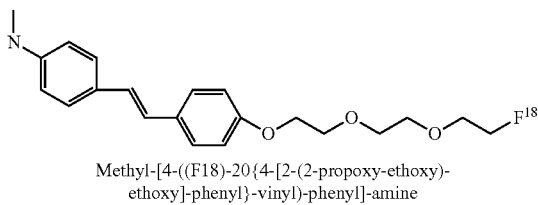

Methyl-[4-((F18)-20{4-[2-(2-propoxy-ethoxy)-ethoxy]-phenyl}-vinyl)-phenyl]-amine In a fourth aspect, the invention is directed to the use of the pharmaceutical formulations of the present invention for the manufacture of a suitable PET imaging formulation for parenteral administration to mammals.

In a fifth aspect, the invention is directed to the use of the pharmaceutical formulations of the present invention for the manufacture of a suitable radiotherapy medicament for parenteral administration to mammals.

In a sixth aspect, the inventors have found a method for obtaining pharmaceutical formulations pursuant to the invention that can be easily integrated into the pharmaceutical processes conducted by automated devices known in the art.

The method for the preparation of a sterile filtered pharmaceutical formulation comprises the steps of:
  Obtaining a radiotracer via an automated device for pharmaceutical use,
  Purification of the radiotracer using solid-phase-extraction cartridges or columns, wherein the radiotracer is eluted with a composition comprising ethanol, optionally solubilisation of radiotracer in ethanol,
  Adding the ethanol eluant into a mixture of polyether, ascorbic acid, and sodium ascorbate for obtaining the pharmaceutical formulations of the present invention and
  Sterile filtration of the pharmaceutical formulation according to the present invention.

The radiotracer is preferably a lipophilic Amyloid beta ligand stilbene according to the general Formula A, and the Figures 1 and 2, and more preferably Methyl-[4-(($^{18}F$)-2-{4[2 (2-ethoxy-ethoxy)-ethoxy]-phenyl}-vinyl)-phenyl]-amine, and ethanol, polyether, ascorbic acid, and sodium ascorbate as defined above.

The sterile filter is a polytetrafluoroethylene (PTFE) or Polyvinylidene Fluoride (PVDF) sterile filter. Preferably, the sterile filter is polytetrafluoroethylene (PTFE) sterile filter.

The invention is also directed to:
  A device for the preparation of the pharmaceutical formulations pursuant to the invention, wherein the radiotracer is preferably obtained via an automated device for pharmaceutical use.

DEFINITIONS

The terms used throughout the entire specification and within the claims of the present invention are defined below but are not limiting the scope of the invention.

"Suitable salts" of the compounds according to the invention include salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

"Suitable salts" of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, diben-zylamine, N-methylmorpholine, arginine, lysine, ethylenediamine and N-methylpiperidine.

"Halogen" means Chloro, Iodo, Fluoro and Bromo. Preferably, halogen means Iodo or Bromo.

The terms "polyether/polyethers" refer to compounds with more than one ether group. In particular, said term refers to polymers which contain the ether functional group in their main chain. While the term generally refers to polymers like polyethylene glycol and polypropylene glycol, low molecular compounds such as the crown ethers may sometimes be included.

In this regard, the term "glycol" refers to low to medium range molar mass polymers.

A "pharmaceutical or radiotracer" is a compound suitable for use in medical applications such as nuclear imaging, chemotherapy and the like. Pharmaceuticals are generally provided in a pharmaceutically-acceptable carrier. PET tracer is a radiotracer.

A "suitable pharmaceutical formulation" is rendered suitable for pharmaceutical use by adjusting the pH, concentration or other physical characteristics of pharmaceutical preparation well known in the art.

The expressions "chemically stable, stability" in accordance with the present invention reflects a concentration interval of the compounds according to general Formula A and compounds according to the Figure 1 or 2 or a mixture thereof or suitable salts thereof as claimed for the provided pharmaceutical formulations of at least 95% to 105%, preferably 98% to 105% after at least 12 hours storage relative to the respective concentration after preparation pursuant to the invention, further characterized in that the respective solutions remain clear without any visible particles after said at least 12 hours storage. The term "concentration interval of compound 2" as used herein is corrected for the decay of fluorine-18.

Further, the expressions "chemically stable, stability" in accordance with the present invention refer to pharmaceutical formulations comprising the compound according to Figure 2, characterized in that said formulations provides the compound 2 with a radiochemical purity of >93%, preferably >95%.

The term "storage" refers to storage conditions from 0° C. to 40° C., preferably, to storage conditions from 10° C. to 40° C., more preferably to ambient storage conditions of 25+/−10° C. The terms "parenteral/parenterally" refer to the introduction of a medication or pharmaceutical formulation pursuant to the invention into the subject or patient to be administered for PET imaging via a route other than the gastro-intestinal tract, in particular via infusion intravenously, injection or implantation.

Unless otherwise specified, when generally referring in the specification and the accompanied claims to "compound/compounds" or "compound/compounds" of Formula A, and the Figures 1 and 2 according to the present invention as well as when referring to any pharmaceutical composition or formulation thereof in the specification and the accompanied claims per se all of the corresponding hydrates, solvates, salts, and complexes thereof are included.

Abbreviations

| | |
|---|---|
| GBq | Giga Becquerel |
| RT | Room Temperature |
| PBS | Phosphate buffered saline |
| PET | Positron Emission Tomography |
| WFI | water for injection |

EXPERIMENTAL DATA

Example 1

Compounds 1 (Fluoro-Labeled) and 2 (Fluoro-Radiolabeled)

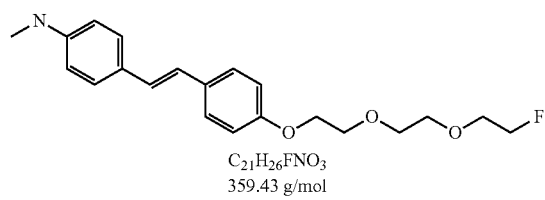

Compound 1

$C_{21}H_{26}FNO_3$
359.43 g/mol

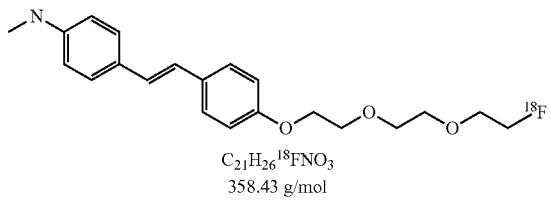

Compound 2

$C_{21}H_{26}{}^{18}FNO_3$
358.43 g/mol

Example 2

Formulations Comprising Lipophilic Amyloid Beta Ligand Stilbene

General Procedure

To mimic the manufacturing procedure in the radio pharmacy department the following procedure was developed.

Formulation 1 Containing Compound 1:

Ascorbic acid and sodium ascorbate were weighed together. Then, water and PEG were added and the mixture was stirred. The lipophilic Amyloid beta ligand stilbene compound 1 was weighted and dissolved in ethanol. This solution was added to the mixture of polyether, ascorbic acid, sodium ascorbate and water and the preparation was mixed.

| Ingredients | Formulation 1 |
|---|---|
| Compound 1 | 30 μg |
| Ethanol 96% | 1.5 mL |
| Polyethylene glycol (PEG 400) | 2 g |
| Ascorbic acid | 0.044 g |
| Sodiumascorbate | 0.288 g |
| Water | ad 10 mL |
| pH | approx. 5.5 |

Since solutions of stilbene are sensitive to light, the solutions were stored under light protection.

Example 3

Stability of Formulation 1 Comprising HCl Salt of Compound 1 for 12 Hours at Room Temperature (RT)

Formulation 1 was prepared containing 3 μg/mL of Compound 1 (according to 3.3 μg/mL HCl salt of compound 1). The assay was analysed after preparation and after 12 hours storage according to the short shelf life of PET imaging tracer, typically expected between 6 and 10 hours. Eight individual batches were prepared and analysed for assay.

Table 1 indicates the results of stability testing after 12 hours of n=8 individually manufactured batches.

TABLE 1

Content of Compound 1 after 12 h storage at three different storage conditions

| Storage condition | n | Visual Inspection | prior filtration | Content of Compound 1 in % after 12 h (min.-max.)[1] after filtration (Minisart HY 0.2 μm) | $\Delta_{Filtration}$ in % (min.-max.) |
|---|---|---|---|---|---|
| RT | 8 | clear solution, no visible particles | 98.9 (97.4-100.1) | 97.0 (95.6-97.8) | 1.9 (1.4-2.6) |

[1]concentration after 12 hours relative to the respective concentration after preparation which was in a range of 2.97 to 3.14 μg/mL.

Minisart HY 0.2 μm is a sterile filter with PTFE hydrophobic membrane.

The assay of compound 1 stays within the 95% to 105% interval within 12 hours observation time and there is no trend of a reduction over time. Compound 1 can be considered to be chemically stable in the formulation.

Example 4

Hydrophobic Filters and Adsorption

Formulation 1 comprising compound 1 was prepared as indicated above and filtered using selected sterile filters. Adsorption of compound 1 was determined by measuring the concentration of Compound 1 before and after filtration of 10 mL of Formulation 1 and subsequent calculation of the adsorption. Table 2 indicates the results of adsorption experiments using different filters.

TABLE 2

Compound 1 filter adsorption (n = 6)

| | Minisart$^{High\ Flow}$ 0.2 μm (Sartorius Stedim) | Pall HP2002 0.2 μm (Pall) | Millex GV 0.22 μm (Millipore) | Minisart HY 0.2 μm (Sartorius Stedim) | Minisart SRP25 0.2 μm (Sartorius Stedim) |
|---|---|---|---|---|---|
| Order No | 16532 | HP2002 | SLGV033RS | 16596-HYK | 17575 |
| Filter membrane | Polyether-sulfone hydrophobic | Versapor ® R hydrophobic | PVDF hydrophobic material that was rendered hydrophilic by surface modification. | PTFE hydrophobic | PTFE hydrophobic |
| Filtrate (%) | 63.9 ± 1.8 | 85.8 ± 0.3 | 94.0 ± 0.7 | 98.8 ± 0.6 | 99.4 ± 0.3 |
| Adsorption | 36.1% | 14.2% | 6.0% | 1.2% | 0.6% |

Only the filter units containing PTFE and PVDF show a low amount of compound 1 adsorbed onto the filter material.

Example 5

Adsorption and Formulation Composition Using Compound 1

Formulation 1 was prepared as described in Example 2. Formulation 2 and Standard Formulation were analogically prepared to the method described in Example 1.

TABLE 3

Composition of formulations tested

| | Formulation 1 | Formulation 2 | Standard Formulation |
|---|---|---|---|
| Compound 1 | 30.0 μg | 30.0 μg | 30.0 μg |
| Ethanol 96% | 1.5 ml | 1.5 ml | 1.5 ml |
| Ascorbic acid | 0.044 g | 0.044 g | — |
| Sodium ascorbate | 0.288 g | 0.288 g | — |
| PEG 400 | 2.0 g | — | — |
| Isotonic saline solution | — | — | 8.5 ml |
| PBS solution | — | — | 50 μl |
| WFI | ad 10 ml | ad 10 ml | ad 10 ml |
| pH | 5.5 | 5.1 | 7.3 |

TABLE 4

Filter adsorption of different formulations using Minisart HY filter (art.no. 16596-HYK), n = 6

| | Formulation 1 | Formulation 2 | Standard Formulation |
|---|---|---|---|
| Filtrate (%) | 98.8 ± 0.6 | 74.7 ± 6 | 42.8 ± 2.4 |
| Adsorption | 1.2% | 25.3% | 57.2% |

TABLE 5

Filter adsorption of different formulations using Millex GV filter (art.no.SLGV033RS), n = 6

| | Formulation 1 | Formulation 2 | Standard Formulation |
|---|---|---|---|
| Filtrate (%) | 94.0 ± 0.7 | 55.9 ± 2.3 | 40.8 ± 0.8 |
| Adsorption | 6.0% | 44.1% | 59.2% |

The invention claimed is:
1. A pharmaceutical formulation comprising:
 0.03 GBq/mL to 5 GBq/mL of Compound 2 of the following formula having an $^{18}F$ fluoro radioisotope group:

Compound 2

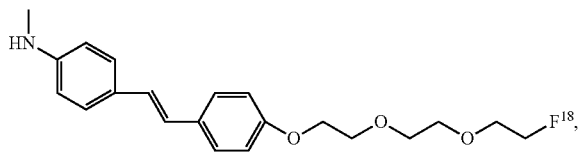

8% v/v to 25% v/v of ethanol,
10% w/v to 25% w/v of poly(ethylene glycol),
0.01% to 3% w/v of ascorbic acid, and
0.01% to 20% w/v of sodium ascorbate.

2. The pharmaceutical formulation according to claim 1 comprising:
0.03 GBq/mL to 5 GBq/mL of Compound 2,
15% v/v of ethanol,
20% w/v of PEG 400 poly(ethylene glycol),
0.44% w/v of ascorbic acid, and
2.88% w/v of sodium ascorbate.

3. A pharmaceutical formulation comprising:
0.01 µg/mL to 5 µg/mL of Compound 2 of the following formula having an $^{18}$F fluoro radioisotope group:

Compound 2

8% v/v to 25% v/v of ethanol,
10% w/v to 25% w/v of poly(ethylene glycol),
0.01% to 3% w/v of ascorbic acid, and
0.01% to 20% w/v of sodium ascorbate.

4. The pharmaceutical formulation according to claim 3 comprising:
3 µg/mL of Compound 2,
15% v/v of ethanol,
20% w/v of PEG 400,
0.44% w/v of ascorbic acid, and
2.88% w/v of sodium ascorbate.

\* \* \* \* \*